(12) United States Patent
Zhu et al.

(10) Patent No.: US 11,692,864 B2
(45) Date of Patent: Jul. 4, 2023

(54) OPEN-TYPE SELF-SERVICE VENDING METHOD BASED ON BUYER POSITIONING, AND SYSTEM

(71) Applicant: NANNING ANPUKANG TRADING CO., LTD., Guangxi (CN)

(72) Inventors: Rijin Zhu, Guangxi (CN); Yuwei Lai, Guangxi (CN)

(73) Assignee: NANNING ANPUKANG TRADING CO., LTD., Nanning (CN)

( * ) Notice: Subject to any disclaimer, the term of this patent is extended or adjusted under 35 U.S.C. 154(b) by 101 days.

(21) Appl. No.: 17/139,723

(22) Filed: Dec. 31, 2020

(65) Prior Publication Data

US 2021/0199489 A1 Jul. 1, 2021

Related U.S. Application Data

(63) Continuation of application No. PCT/CN2019/095267, filed on Jul. 9, 2019.

(30) Foreign Application Priority Data

Jul. 9, 2018 (CN) .......................... 201810747411.5

(51) Int. Cl.
| | | |
|---|---|---|
| *G01G 19/414* | (2006.01) | |
| *A61L 9/20* | (2006.01) | |
| *G06Q 20/18* | (2012.01) | |
| *G06Q 20/20* | (2012.01) | |
| *G06Q 20/32* | (2012.01) | |

(52) U.S. Cl.
CPC ............ *G01G 19/4144* (2013.01); *A61L 9/20* (2013.01); *G06Q 20/18* (2013.01); *G06Q 20/203* (2013.01); *G06Q 20/208* (2013.01); *G06Q 20/3278* (2013.01); *A61L 2209/111* (2013.01); *A61L 2209/212* (2013.01)

(58) Field of Classification Search
CPC . G01G 19/4144; A61L 9/20; A61L 2209/111; A61L 2209/212; G06Q 20/18; G06Q 20/203; G06Q 20/208; G06Q 20/3278; A47F 9/04; A47F 2009/041
See application file for complete search history.

(56) References Cited

U.S. PATENT DOCUMENTS

| | | | | |
|---|---|---|---|---|
| 5,497,853 | A | * 3/1996 | Collins, Jr. ..........| G07G 1/0054 235/383 |
| 11,308,442 | B1 | * 4/2022 | Kumar .................| G01G 19/42 |

(Continued)

FOREIGN PATENT DOCUMENTS

| | | |
|---|---|---|
| CN | 104361693 A | 2/2015 |
| CN | 105678925 A | 6/2016 |

(Continued)

*Primary Examiner* — Sonji N Johnson

(57) ABSTRACT

An open self-service sales system based on positioning of customers includes an open partitioned weight-sensing rack including multiple storage subareas. The open self-service sales system further includes a positioning module and an automatic weighing unit which are connected to the central control module. The position information of the customer is bound with the subareas to accurately identify customers and the purchasing behaviors. The data flow is simple and reliable, and a large number of computing is avoided, which is suitable for large customer flows.

19 Claims, 2 Drawing Sheets

(56) References Cited

U.S. PATENT DOCUMENTS

| | | | |
|---|---|---|---|
| 2007/0210154 A1 | 9/2007 | Suto | |
| 2013/0223673 A1* | 8/2013 | Davis | G06Q 20/208 |
| | | | 235/375 |
| 2015/0187160 A1* | 7/2015 | Anning | G07F 9/026 |
| | | | 700/231 |
| 2019/0149725 A1* | 5/2019 | Adato | G06V 20/17 |
| | | | 348/158 |
| 2020/0184442 A1* | 6/2020 | Gu | G06Q 20/208 |
| 2020/0202137 A1* | 6/2020 | Li | G01G 19/52 |

FOREIGN PATENT DOCUMENTS

| | | | | |
|---|---|---|---|---|
| CN | 107424340 A | 12/2017 | | |
| CN | 108205853 A | 6/2018 | | |
| CN | 207558078 U | 6/2018 | | |
| CN | 108921540 A | 11/2018 | | |
| JP | 6342039 B1 * | 6/2018 | | |
| WO | WO-2018117955 A1 * | 6/2018 | ........... | B62B 5/0096 |

\* cited by examiner

OPEN-TYPE SELF-SERVICE VENDING METHOD BASED ON BUYER POSITIONING, AND SYSTEM

CROSS-REFERENCE TO RELATED APPLICATIONS

This application is a continuation of International Patent Application No. PCT/CN2019/095267 with a filing date of Jul. 9, 2019, which claims the benefit of priority from Chinese Patent Application No. 201810747411.5 with a filing date of Jul. 9, 2018. The content of the aforementioned applications, including any intervening amendments thereto, is incorporated herein by reference.

TECHNICAL FIELD

The present application relates to sales equipment, and in particular to an open self-service sales method and an open self-service sales system based on positioning of customers.

BACKGROUND

Generally, customers are required to weigh products at specified scales in traditional agricultural trade markets and supermarkets, so as to price them by category. This increases sales labor costs. In addition, the customer needs to queue to weigh products, which affects the shopping experience. In some unmanned supermarkets, quick-response (QR) codes or radio frequency (RF) labels should be attached on items in advance for pricing, which increases the workload and cost of delivery. In some machine-vision based unmanned supermarkets, when there is a large flow of people, purchase behaviors of customers cannot be accurately recognized due to settings and recognition rates of cameras, and computing loads of systems.

SUMMARY OF THE DISCLOSURE

The present disclosure aims to provide an open self-service sales method and an open self-service sales system based on positions of customers. After the selection of products is completed, the quantity of products selected by the customer is automatically calculated through automatic weighing units corresponding to storage subareas of different products. Purchase behaviors are automatically identified based on the real-time positions of the customer, and the quantity and the amount of the selected products are sent to an account of the customer for settlement. This causes a simplified shopping process, shortened queuing time, and reduced cost, so that open and automatic shopping is realized.

The present disclosure provides an open self-service sales method based on positioning of customers, comprising:

placing products in different storage subareas by category, wherein each of the storage subareas has a unique ID code, and each customer has unique characteristic information when entering a store;

when the customer shops in a storage subarea, automatically weighing the products in the storage subarea before and after shopping through an automatic weighing unit located at a bottom of the storage subarea, respectively; calculating the quantity of selected products to generate current shopping quantity information, wherein the current shopping quantity information comprises the quantity of the selected products and an ID code of the storage subarea;

acquiring a real-time position of the customer; determining whether the customer is shopping according to a distance between the customer and the storage subarea; if yes, generating current customer information comprising the unique characteristic information of the customer and the ID code of the storage;

acquiring the real-time position of the customer; determining whether the customer has stopped shopping according to the distance between the customer and the storage subarea; if yes, determining that the current shopping quantity information of the customer is valid;

calculating the amount of products corresponding to the current quantity information of the customer according to a unit price of the products pre-stored in the storage subarea; generating current shopping amount information comprising the amount of products and the ID code of the storage subarea;

establishing a relationship between the current shopping quantity information, the current customer information and the current shopping amount information according to the ID code of the storage subarea; and generating current shopping information;

accumulating unsettled current shopping information according to the unique characteristic information of the customer to generate a shopping list; sending the shopping list to the customer, wherein the shopping list comprises the order number, time, a product name, a unit price, the quantity, the amount and the total amount of the products selected by the customer; and paying for the products in the shopping list using cash, e-banking or a third-party payment platform, and letting a guard device open to allow the customer to leave.

When a weight of the open self-service sales system changes, images of the storage subarea are collected by frame, and a relationship between the time when the weight of the storage subarea changes and the time when the images of the storage subarea are collected is established; and whether a product that the customer picks on the storage subarea is consistent with the product that the customer returns is identified using a machine vision technology to avoid abnormal exchanges.

The storage subarea has a sales state, a restock state and a return state; when the storage subarea is in a restock state, the current shopping quantity information of the customer is not generated; the open self-service sales system monitors the weight of the products in real time; when the weight of the products is close to the limit of weighing, the open self-service sales system issues an over-range warning; the storage subarea returns to the sales state after restocking is over; and when the storage subarea is in the return state, the current shopping amount information is determined to be invalid, and the customer is notified.

The automatic weighing unit has an over-range alarm function; when the weight of the products is equal to or exceed a preset range of the automatic weighing unit, the automatic weighing unit issues a prompt or an alarm.

The present disclosure further provides an open self-service sales system based on positioning of customers, comprising:

an open partitioned weight-sensing rack;
a positioning module configured to detect the position of the customer;
a pricing module;
a settlement module;
an access control unit; and
a central control module;

wherein the open partitioned weight-sensing rack has a plurality of storage subareas, and an automatic weighing unit is provided at a bottom of each of the storage subareas; a shopping subarea is provided in front of each of the storage subareas and the positioning module, the automatic weighing unit, the pricing module, the settlement module, and the access control unit are connected to the central control module, respectively. The open partitioned weight-sensing rack and the positioning module adopts a weight sensing technology and a high-precision indoor positioning technology to automatically identify shopping behaviors of customers. Specifically, information, such as shopping personnel, product category, product quantity (weight) and shopping time are detected.

The open partitioned weight-sensing rack mainly has functions of loading, displaying, and automatically weighing goods; calculating the weight or the quantity of purchased products; and notifying customers of pricing information. The open partitioned weight-sensing rack includes an automatic weighing unit, a control unit, a client interface, a purchase isolation device, and an intelligent disinfection unit. The open partitioned weight-sensing rack is designed to be modularized, facilitating the mounting and the combined assembly.

The automatic weighing unit weighs the products placed on it in real time for pricing. The open self-service sales system can automatically identify the weight or the quantity of the products through pre-stored features such as the unit weight of the products, the total weight of the products, and the packaging information.

customer from the storage subarea through weight changes. The open self-service sales system calculates the limit of the number of different single products to prevent the situation where a total weight is a common multiple of weights of the different single products and the picked products are not accurately identified.

The control unit provides micro-computing support for the storage subarea, and is configured for control, communication and storage. The storage subarea communicates with the central control module of the open self-service sales system through the control unit, transmits data, and receives instructions from the central control module. One control unit is capable of controlling multiple weighing platforms.

The open self-service sales system further comprises a client interface comprising a voice broadcast module, a display screen, an intelligent display tag and a status indicator; the status indicator emits lights of different colors and flashes in different modes to indicate that the shopping subarea is in different modes. The client interface is connected to the central control module. The status indicator can be but not limited to an LED strip to show the status of the storage subarea. Interactive information such as the name, a quantity, a unit price, a total price of the products selected by the customer are displayed in real time, so as to realize electronic tags of the products. An alarm is issued through the client interface when there are abnormal weight changes of the products When multiple people are in the same storage subarea, and there are other abnormalities, the client interface displays relevant information to remind customers. The reminder information is shown in Table 1.

TABLE 1

Information shown in the client interface

| State of the storage subarea | Measures | Displayed information |
| --- | --- | --- |
| No customer shopping in the shopping subarea | Take client interface as an electronic product tag | Information such as descriptions, prices and discounts of products |
| One customer shopping in a shopping subarea | The customer is in a normal shopping state | Shopping information such as customer ID, real-time quantity and amount of purchased products |
| One customer leaves after the shopping is finished | Price for the current shopping | Price information, such as quantity and amount of the current shopping, and remind the completion of the shopping |
| Multiple customers in a storage subarea | An ID card that first enters the storage subarea be in a shopping state | ID of the customer in the shopping state and remind the customer that there are multiple customers in the storage subarea |
| Abnormal weight changes | Treated as abnormality | Abnormal weight change information and issue a warning |
| Only one customer is in the storage subarea, and weights of the racks (boards) change simultaneously | Determine the customer picks products on different racks simultaneously; record in the shopping list; and remind the customer through the client interface | Remind that the customer is picking products from multiple racks (boards); and display real-time quantity and amount of picked products |
| A staff member enters the storage subarea, or the customer is returning products of this storage subarea | Restock/return | Real-time weight/quantity for restock/return |

Automatic weighing units with different specifications may be equipped with storage subareas of different specifications to display various products. Products with different weights can be placed in the same storage subarea, and the system can automatically identify the products picked by the The purchase isolation device is isolation baffles with an interval of 0.4-1.5 m; the isolation baffles are respectively mounted at two sides of the storage subareas, and each of the isolation baffles is 0.03-0.8 m higher than products. The arrangement of the purchase isolation device is to prevent customers to pick up products from adjacent storage areas, so as to ensure the accurate attribution of purchase behaviors in each of the storage subareas.

The ID held by a restocking worker is detected to let the storage subarea be in the restocking mode. At this time, the automatic weighing unit does not generate shopping quantity information and send it to the central control module. After the restocking, the open self-service sales system is reset to a sales state, and the weight of the products is updated.

The machine vision technology is adopted in the open partitioned weight-sensing rack. When a weight of the storage subarea changes, images of the storage subarea are collected by frame through a camera mounted in the storage subarea, and a relationship between the time when the weight of the storage subarea changes and the time when the images of the storage subarea are established; and machine vision technology is adopted to identify whether a product that the customer picks on the storage subarea is consistent with the product that the customer returns. When a product is placed in a storage subarea to which the product does not belong, the central control module guides workers to deal with it in time.

The positioning module is an indoor wireless positioning technology based device comprising at least one of a mobile positioning device, a Wi-Fi positioning device, a machine vision device, a radio frequency identification (RFID) read and write device, an ultra-wideband (UWB) positioning base station, a Bluetooth positioning receiving device, an infrared positioning receiving device and an ultrasonic positioning receiving device. The positioning module has the following features.

The positioning module is capable of accurately identifying customers entering or leaving the shopping subarea. When the customer does not enter the storage subareas, the identification is not necessary, which saves computing resources of the open self-service sales system. The positioning module is configured to identify the real-time position of the customer and determine whether the customer is shopping in the open partitioned weight-sensing rack according to a relationship between the real time position of the customer and stay time of the customer at a current position. The positioning module determines whether the customer is shopping in the open partitioned weight-sensing rack according to a two-dimensional algorithm of the real-time position of the customer and stay time of the customer at a current position.

The positioning module can ensure the density of the people flow in the supermarket to be 0.2~0.4 person/$m^2$, and multiple ID cards in the antenna working area can be identified. When multiple people enter the same storage subarea at the same time, the positioning module can determine the entry order and the distance between the customers and the rack. The system intends to first take the customer that enters an area having an effective distance within 0.3 meters from the storage subarea and stays for more than 3 seconds as the current shopping customer.

The positioning module based recognition can overcome the interference of supermarket personnel, the storage subareas, and products.

The positioning module can identify abnormal exit tags, and only customers who have settled the shopping list are allowed to leave from exit gates after returning their ID chips, and other people who attempt to carry their ID chips can be identified.

The positioning module can remotely read the information (tags) of the customers entering the storage subarea to identify the customers. Security authentication and privacy protection are ensured in the information transmission process to avoid illegal access and forged labels.

The positioning and the machine vision (face recognition) are adopted for the verification, which can accurately verify the identity of the customer and detect the real-time position of the customer, so as to prevent customers from stealing ID chips of other customers, thereby improving the safety.

The visual recognition unit of the storage subarea also records the video of customers shopping and picking up products, which can be used as evidence when disputes occur.

The open self-service sales system further comprises an identity chip which is configured to identify the real-time position of the customer; the ID chip is carried by the customer, or the customer carries a shopping container on which the ID chip is attached.

In an embodiment, a plurality of ID chips are arranged on the shopping container at different positions, so that the ID chips can be better identified by the positioning module.

In an embodiment, the shopping container may be a shopping basket or a shopping cart.

When the customer shops in the storage subarea, the pricing module calculates the quantity of products purchased by the customer according to the weight of the products obtained from the storage subarea, so as to generate the current shopping quantity information. The current shopping quantity information comprises the quantity of the selected products and the ID code of the storage subarea. At the same time, the position of the customer is obtained. Whether the customer is shopping is determined according to a distance between the real-time position of the customer and the storage subarea; if yes, current customer information comprising the unique characteristic information of the customer and the ID code of the storage subarea is generated. The real-time position of the customer is acquired. Whether the customer has stopped shopping is determined according to the distance between the customer and the storage subarea; if yes, the current shopping quantity information of the customer is determined to be valid. The amount of products corresponding to the current quantity information of the customer is calculated according to a unit price of the products pre-stored in the storage subarea. Current shopping amount information comprising the amount of products and the ID code of the storage subarea is generated. A relationship between the current shopping quantity information, the current customer information and the current shopping amount information is established according to the ID code of the storage subarea to generate current shopping information.

Based on the unique characteristic information (binding with an RFID tag card) of the customer, unsettled current shopping information is accumulated to generate a shopping list. A QR code is fixed on each tag, so that the card and the code are integrated. After the customer finishes shopping, the QR code on the tag is scanned using the mobile phone to obtain the shopping list. The shopping list comprises the order number, time, a product name, a unit price, the quantity, the amount and the total amount of the products selected by the customer. The customer pays for the products in the shopping list using cash, e-banking, a third-party payment platform, or a gift card. After the settlement, a guard device is opened to allow the customer to leave.

The self-service sales system further comprises a plurality of client interfaces connected to the central control module, and each of the storage subarea is provided with a client interface. The positioning module recognizes the real-time position of a person through the ID chip carried by the person, and identifies the identity through the ID chip carried by the person, and judges whether the person is a customer or a staff member, so as to carry out normal procedures of purchases, restocking or return.

The open self-service sales system further comprises an access control unit. The access control unit combines machine vision and indoor wireless positioning technology, and an archive containing an identity of the customer and an ID card corresponding to the identity of the customer is established in an entrance channel, and the checking is randomly performed in the store by using the face recognition technology to prevent the customer to change the ID chips. A channel for regular customers and a channel for new customers are provided at an entrance, or the regular customers and the new customers are automatically identified, so as to provide the new customers with a training video comprising a shopping operation procedure and a training picture to allow the customer to know the shopping operation procedure.

The open self-service sales system further comprises the access control unit comprising an entry passage, an exit passage and an ID chip collection and issue module. The entry passage and the exit passage are formed through the passage isolation device and a gate. An entrance and an exit of the entry passage are formed by the blocking bodies at both ends of the entry passage, and an entrance and an exit of the exit passage are formed by the blocking bodies at both ends of the exit passage. The access control unit controls the block bodies to block the customer or let the customer pass. The ID chip collection and issue module is configured to issue and collect an RFID tag, a UWB tag, a Bluetooth positioning signal source tag, an infrared positioning signal source tag, or an ultrasonic positioning signal source tag, and issue and collect the ID chip and a shopping container attached with the ID chip. the access control unit controls the block bodies to block the customer or let the customer pass according to issue and collection of the ID chip and a payment state corresponding to the ID chip, or issue and collection of the shopping container attached with the ID chip and a payment state corresponding to the shopping container attached with the ID chip; and the access control unit is configured to remind the customer to perform corresponding operations. The ID chip and the shopping container attached with the ID chip are recyclable. The ID chip may be a passive card or an active card, and the passive card can be automatically charged.

After completed shopping, pricing, settlement and payment, the customers can exit through the control gates. The customer inserts the ID chip into the control gate, or the shopping container attached with the ID chip is placed or pushed into the control gate. The open self-service sales system confirms that there is no unpaid bill relating to the ID card, and then verifies whether the ID chip matches the face image of the customer. If the verification is passed, the gate is opened to allow the customer to leave. Customers who have no ID chip tag (card) are not allowed to leave.

The VIP ID chips are provided to the regular customers and directly swiped to enter the store. For customers who have a pre-deposited amount in the ID chip, the open self-service sales system can automatically perform the settlement and send the settlement list to the customer's mobile phone. The customers can directly swipe their ID chips to go out after shopping.

The open self-service sales system has two return methods. One is that when the storage subarea is in the return state, the customers place the products back to the original storage subarea. Then, the open self-service sales system confirms and deletes the products picked by the customer, i.e., when the customer is shopping in a storage subarea, the picked products can be returned to the storage area. The open self-service sales system establishes a relationship between the time when the weight of the storage subarea changes and the time when the images of the storage subarea are collected. The machine vision technology is adopted to identify whether the returned product is consistent with the picked product (not priced). If yes, the open self-service sales system will automatically deletes the returned goods from the shopping list of the customer; otherwise, it is determined to be an abnormal product, and an abnormal alarm is issued. The other method is to return the product in a special return desk, in which the returning is guided by the service worker, i.e., after the worker confirms the ID of the customer and the information of returned product, the shopping list is updated through the open self-service sales system. Specifically, the central control module of the open self-service sales system or the calculation module of the rack are adopted to identify and confirm the products purchased by the customer, and delete the products purchased by the customer through the central control module.

A shape and a size of the shopping subarea on the automatic weighing unit correspond to that of the storage subarea.

Through the open self-service sales system, weights of different products correspond to their warranty periods. The open self-service sales system can track the warranty periods of the remaining products in the storage subarea at any time, and can prompt the management staff about the products near the warranty period.

The open self-service sales system further comprises an intelligent disinfection unit; wherein the intelligent disinfection unit is mounted around the storage subarea; when positioning module detects that there is no person in the shopping subarea, the products in the storage subarea are disinfected by ultraviolet rays or ozone through the intelligent disinfection unit; and when the positioning module detects that a person is close to the shopping subarea, the intelligent disinfection unit automatically stops the disinfection of the products.

Specifically, the open self-service sales method comprises the following steps.

The customer enters the store through the entrance gate, and receives the ID chip or the shopping container attached with the ID chip from the automatic card issuing machine as the unique characteristic information of the customer. At the same time, the visual recognition unit acquires the visual characteristics of the customer, and a relationship between the ID chip and the visual characteristics of the customer is established.

The customer selects products freely, and the positioning module determines the storage subarea where the customer is located in real time, whether the customer is shopping, and the ID of storage subarea.

The customer picks up the product to be purchased, and the automatic weighing unit calculates the quantity and category of the picked product according to the weight change.

The pricing module calculates the amount of the products selected by the customer in real time.

The client interface displays information such as the name, the quantity, the unit price, and the total price of the products that the customer has selected.

After the selection of the products is completed, payment can be made through various methods such as mobile phone, cash, and prepaid cards, so as to realize the quick payment.

Customers who have completed the payment return the ID chips or the shopping containers attached with the ID chips through the exit gates to complete the entire shopping process.

The present invention has the following advantages.

(1) The customers and the purchase behaviors can be accurately identified.

A unique relationship is established between the shopping subarea (the storage subarea) and the information of the customer. The quantity of the selected products is accurately counted by weight, which improves the accuracy of customer information and the identification of purchase behaviors.

(2) The data flow is simple and reliable, and a large number of computing is avoided, which is suitable for large customer flows.

Since the customer's purchase behavior is confirmed by hardware, the amount of data computing is small, which greatly saves computing resources of the open self-service sales system, and is suitable for use in complex scenarios and dense crowds.

(3) Open restocking and shopping can be completed at one time without additional processes such as adding tags and price checking. Customers freely purchase products, in which real-time automatic accounting is realized, and the customer pays for the selected products at one time. Thus, merchants and customers have excellent shopping experiences based on the open self-service sales system and the open self-service sales method.

Figure 1:
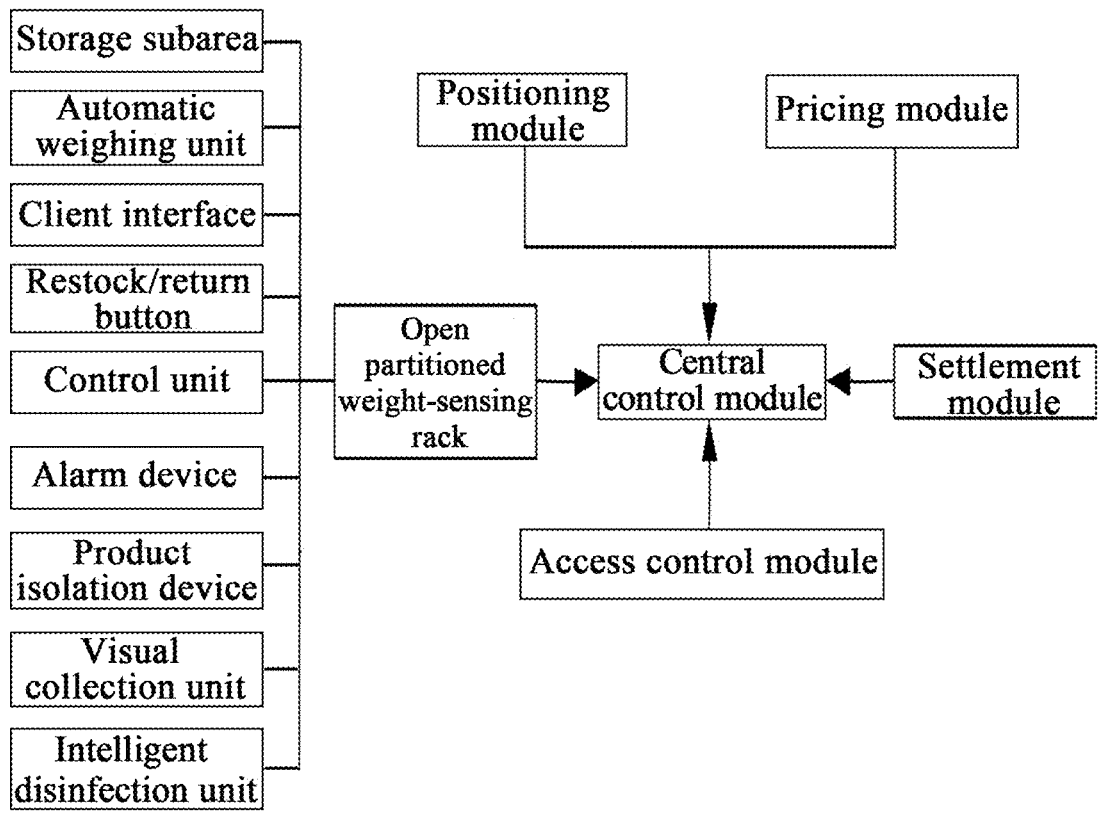
FIG. 1 is a schematic diagram of an open self-service sales system based on positioning of customers according to an embodiment of the present disclosure.

In the drawings: 1, storage subarea; 2, automatic weighing unit; 3, purchase isolation device; 4, visual collection unit; 5, client interface; 6, intelligent display tag; 7, status indicator; 8, product; 9, control unit; 10, shopping subarea; 11, RF low-frequency antennal (125 KHz); 12, RF low-frequency activator; 13, visual recognition unit of the storage subarea; 14, RF high-frequency reader; 15, network switch; 16, positioning computing center; 17, intelligent disinfection unit; 18, RF card.

DETAILED DESCRIPTION OF EMBODIMENTS

The embodiments of the present disclosure will be described in detail below with reference to the accompanying drawings, and are not intended to limit the scope of the present disclosure.

The present disclosure provides an open self-service sales method based on positioning of customers. Products 8 are placed in different storage subareas 1 by category, and each storage area 1 corresponds to a unique ID code, and each customer has unique characteristic information when entering a store.

When the customer shops in a storage subarea 1, the storage subarea 1 before and after shopping is automatically weighed through an automatic weighing unit 2 located at a bottom of the storage subarea 1, respectively. The quantity of selected products is calculated to generate current shopping quantity information. The current shopping quantity information includes the quantity of the selected products and an ID code of the storage subarea 1. At the same time, a real-time position of the customer is acquired, and whether the customer is shopping is determined according to a distance between the real-time position of the customer and the storage subarea. If yes, current customer information including the unique characteristic information of the customer and the ID code of the storage is generated. Then the real-time position of the customer is acquired, and whether the customer has stopped shopping is determined according to the distance between the customer and the storage subarea 1. If yes, the current shopping quantity information of the customer is determined to be valid. The amount of products corresponding to the current quantity information of the customer is calculated according to a unit price of the products pre-stored in the storage subarea 1. Current shopping amount information including the amount of products and the ID code of the storage subarea 1 is generated. A relationship between the current shopping quantity information, the current customer information and the current shopping amount information is established according to the ID code of the storage subarea, and current shopping information is generated.

Unsettled current shopping information is accumulated according to the unique characteristic information of the customer to generate a shopping list. The shopping list is sent to the customer. The shopping list includes the order number, time, a product name, a unit price, the quantity, the amount and the total amount of the products selected by the customer. The products in the shopping list are paid using cash, e-banking or a third-party payment platform. Then, a guard device is opened to allow the customer to leave.

The core of the open self-service sales system is an open partitioned weight-sensing rack which mainly has functions of loading, displaying, and automatically weighing goods; calculating the weight or the quantity of purchased goods; and notifying customers of pricing information. The open partition weight-sensing rack includes a storage subarea 1, an automatic weighing unit 2, a control unit 9, a visual collection unit 4, a client interface 5, a purchase isolation device 3, and an intelligent disinfection unit 17. The open partitioned weight-sensing rack is designed to be modularized, facilitating the mounting and the combined assembly.

Figure 2:
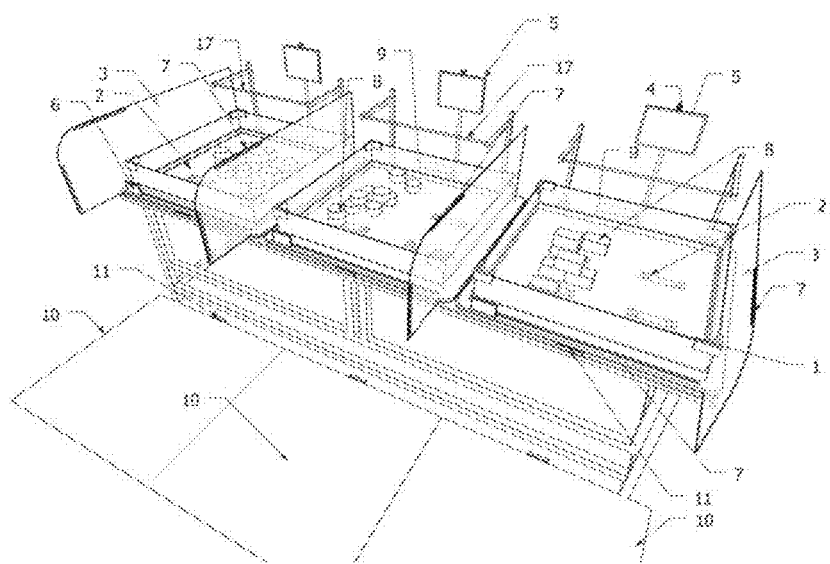
FIG. 2 is a schematic diagram of an open partitioned weight-sensing rack (floor display) of the open self-service sales system according to an embodiment of the present disclosure.
Figures 3, 4:
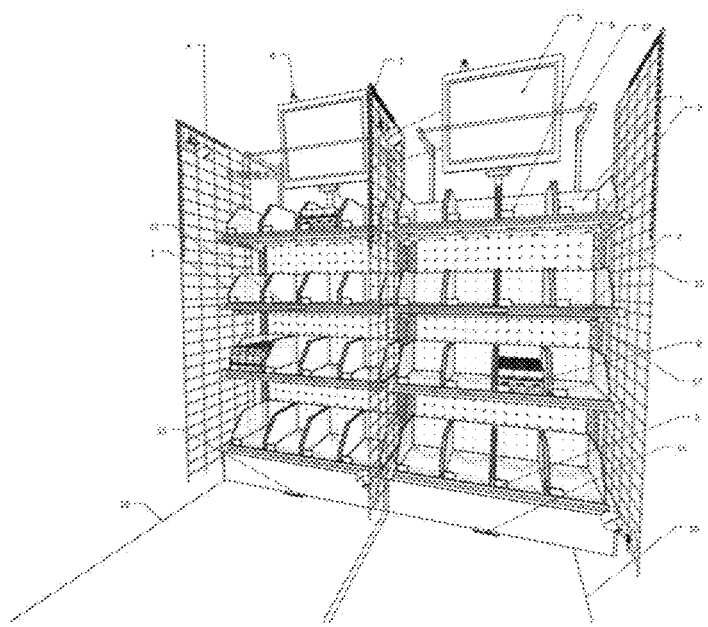
FIG. 3 is a schematic diagram of an open partitioned weight-sensing rack (multi-layer rack) of the open self-service sales system according to an embodiment of the present disclosure.
FIG. 4 shows a network topology and working diagram of the positioning module of the open self-service sales system.

As shown in FIG. 2, the open self-service sales system includes the open partitioned weight-sensing rack which is provided with a plurality of storage subareas 1. Each of the storage subareas 1 corresponds to a unique ID code. The open partitioned weight-sensing rack has various shapes, and may be a special-shaped frame.

The products 8 are placed in different storage subareas 1. An automatic weighing unit 2 is provided at a bottom of each of the storage subareas 1. The storage subarea 1 is automatically weighed in real time through the internal pressure sensor of the automatic weighing unit 2, with an accuracy of C3 (the measurement accuracy is within 0.03%). The automatic weighing unit 2 pre-stores corresponding characteristic information such as unit weight and packaging of the products.

The shopping area is divided into shopping subareas through the purchase isolation device 3. The purchase isolation device 3 includes a plurality of isolation baffles with an interval of 0.4-1.5 m. The isolation baffles are respectively mounted at two sides of the storage subareas 1, and each of the two isolation baffles is 0.03-0.8 m higher than the products. The arrangement of the purchase isolation device 3 is to prevent customers to pick up products from adjacent storage subareas 10, so as to ensure the accurate attribution of purchase behaviors in each of the storage subareas 1 of each shopping subarea 10.

The open self-service sales system further includes a control unit 9. The control unit 9 provides micro-computing support for the open partitioned weight-sensing rack, and is configured for control, communication and storage. The open partitioned weight-sensing rack communicates with the central control module of the open self-service sales system through the control unit 9, transmits data, and receives instructions from the central control module. One control unit 9 is capable of controlling multiple weighing units 2.

A shopping subarea 10 is provided in front of each of the storage subareas 1. The client interface 5 includes a voice broadcast module, a display screen, an intelligent display tag 6 and a status indicator 7; the status indicator emits lights of different colors and flashes in different modes to indicate that the shopping subarea 10 is in different modes. The client interface 5 is connected to the central control module. The status indicator can be but not limited to an LED strip to show the status of the storage subarea. Interactive information such as the name, a quantity, a unit price, a total price of the products selected by the customer are displayed in real time. When there are multiple people in the same shopping subarea, and other shopping abnormalities occur, the client interface displays relevant information to remind the customer. The display screen, the electronic tag, and the status indicator can display the statuses including but not limited to the locked status, the activated status, the shopping status, the promotion status, the measuring status, and the picked status of the storage subarea, and sound an alarm when there are abnormal weight increases.

The open self-service sales system further includes a positioning module, a positioning module, a settlement module, an access control module. A unit price of the products of the storage subarea is pre-stored in the pricing module. The positioning module, the pricing module, the settlement module, and the access control module are connected to the central control module, respectively. In this embodiment, the central control module is a server, and the pricing module and the settlement module are personal computers (PCs), respectively.

A machine vision collection unit 4 adopting a machine vision positioning technology is mounted in each shopping subarea 10.

The positioning module adopts radio frequency identification (RFID) (proximity method) and the machine vision for the verification, which can accurately verify the identity of the customer and detect the position of the customer.

The positioning module includes an RF card 18, an low-frequency activator 12, a high-frequency reader 14, a visual recognition unit 13, and a positioning computing center 16. Specifically, the RF card 18 is a 125 K & 2.4 G semi-active RF card, (z); the RF low-frequency exciter 12 is a 125 K low-frequency exciter; the RF high-frequency reader 14 is a 2.4 GHz high-frequency reader, and RF low-frequency exciter 12 includes an RF low-frequency antenna 11.

The open self-service sales system also includes a network switch 15, and both the RF high-frequency reader 14 and the positioning computing center 16 are electrically connected to the network switch 15. The RF card 18 is the aforementioned ID chip.

The RF card 18 is activated by the RF low-frequency antenna 11 of the storage subarea when the customer carries the RF card 18 to the shopping subarea 10, and obtains the ID of the RF low-frequency antenna 11. After activation of the RF card 18, the tag actively sends the antenna ID and RSSI value (signal strength) to the nearby RF high-frequency reader 14 in the 2.4 GHz frequency band to realize the positioning of the shopping subarea 10 where the customer is located.

The visual recognition unit 13 cooperates with the RFID recognition technology to identify the facial information of customers entering the storage subarea and to compare it with the facial information obtained when the RF card 18 is issued at the entrance to verify the customer information identified by RFID, so as to avoid the mismatching of the RF card and the facial information. The visual recognition unit 13 communicates with the positioning computing center 16 through a wireless network.

The positioning computing center 16 processes and analyzes the information transmitted by the RF high-frequency reader 14 and the visual recognition unit 13 of the storage subarea. After verification and computing, the real-time position information (shopping subarea 10) of the customer is sent to the central control module of the open self-service sales system.

Each customer is allocated with unique characteristic information when entering the store. The open self-service sales system automatically collects the facial information of the customer when the RF card 18 is issued to establish a relationship between the facial information of the customer and the RF card 18, and the checking is randomly performed in the store to prevent the customer to change the RF card 18. The regular customers and the new customers are distinguished through the face recognition technology. Different guide mechanisms are adopted for the regular customers and the new customers to provide excellent shopping experiences. New customers refer to customers who enter the store for the first time, regular customers refer to customers who enter the store twice or more. For the new customers, videos or shopping procedure pictures are displayed to carry out the training. For the regular customers, the open self-service sales system displays friendly welcome information.

The visual collection unit 4, the client interface 5 and the intelligent disinfection unit 17 are mounted in each storage subarea 1. The visual collection unit 4, the client interface 5, the intelligent disinfection unit 17 are respectively connected to the central control module through the control unit 9. Further, the client interface 5 includes an intelligent display tag 6 and a status indicator 7 which are connected to the central control module.

The working process of the open self-service sales system is described as follows.

When a customer selects a product 8 on a storage subarea 1, the corresponding automatic weighing unit 2 calculates the weight change information of the storage subarea 1 by separately weighing the weight of the storage subarea 1 before and after the customer selects the product 8. According to the pre-stored feature information such as the unit weight of the product 8 corresponding to the storage subarea 1 and the weight change information of the storage subarea 1, the quantity of the product purchased by the customer is calculated, and then the current shopping quantity information is generated and sent to the central control module. The current shopping quantity information includes the quantity of selected products and the ID code of the storage subarea 1. At the same time, based on the machine vision and the recognition time, the open self-service sales system verifies the picking behavior by comparing the pictures before and after the customer picks up the products 8.

The positioning module determines whether the customer is in the shopping subarea 10 located in front of the storage subarea 1 by determining the distance between the RF card 18 and the RF low-frequency antenna 11 and whether the RF card 18 carried by the customer is activated by the RF low-frequency activator 12 belong to the shopping subarea 10. If yes, the positioning information of the customer is automatically associated with the storage subarea 1, that is, the unique characteristic information of the customer and the ID code of the storage area are associated to generate the current customer information, and the current customer information is sent to the central control module.

The central control module judges whether the customer has left the storage subarea 1 based on the real-time positioning information of the customer and the storage subarea 1. If the customer leaves, the shopping is over. At this time, the current shopping quantity information is determined to be valid.

The central control module sends the effective current shopping quantity information to the pricing module. The pricing module searches for the unit price of the corresponding product 8 according to the ID code of the storage area in the shopping quantity information and calculates the amount of the selected products, and generates the current shopping quantity information. Then, the current shopping quantity information is sent to the central control module. The current shopping amount information includes the amount of the selected products and the ID code of the storage subarea 1.

A relationship between the current shopping quantity information, the current customer information and the current shopping amount information is established according to the ID code of the storage subarea. Current shopping information is generated and sent to the client interface 5. The client interface 5 informs the customer of the current shopping information in the storage subarea 1 through voice or displays.

The central control module accumulates unsettled valid customer shopping information based on the unique characteristic information of the customer, and generates a shopping list. Then, the shopping list is sent to the settlement module and the mobile phone of the customer.

The settlement module carries out the settlement based on the shopping list sent by the central control module. The settlement module is connected to payment systems such as banks or third-party payment platforms, so that the customer pays for the products in the shopping list using cash, e-banking or the third-party payment platform. After the customer settles, the settlement module sends the settlement information to the central control module. The central control module determines whether the customer is allowed to leave the store according to the settlement situation of the customer, controls the guard devices including gates or exit doors to let the customer leave. The exit prohibition device is a control gate or an exit door.

The ID held by a restock worker is detected to let the storage subarea be in the restocking mode. At this time, the automatic weighing unit 2 does not generate shopping quantity information and send it to the central control module. After the restocking, the open self-service sales system is reset to a sales state, and the weight of the products is updated. In the restocking process, the open self-service sales system monitors the weight of the products in the storage subarea 1 in real time. When the weight of the products is close to a maximum value of the weighing range of the automatic weighing module, the system sends out an over-range warning. When the customer returns the products, and the system identifies that the product is returned correctly, the currently received shopping quantity information is determined to be invalid. The return information is not sent to the pricing module, and the return information is reminded to the customer through the client interface 5. In the case that the system is not in the restock state or the return state, when the automatic weighing unit 2 senses an abnormal weight increase of the products, the client interface 5 issues the alarm to the background through voice. The client interface 5 reminds customers of their shopping information through the display screen and the LED strips. For example, the green LED strip indicates that the current shopping subarea is normal, the red LED strip indicates the current shopping subarea is abnormal, and the yellow LED strip indicates that the current shopping subarea is in a return/restocking status.

The shape and the size of the storage subarea 1 and the automatic weighing unit 2 located below the storage subarea 1 are adjustable, thereby facilitating the category adjustment of products.

The real-time weight of the products in each storage subarea 1 is automatically monitored in the background of the open self-service sales system, and the open self-service sales system is automatically reminded when the products are insufficient.

In the case of taking the face of the customer as the positioning information source, the camera mounted in the entry channel will take a picture of the customer when the customer enters the store, and a unique number is assigned as the unique characteristic information of the customer. The customer is informed through sound, light, receipt, etc. A machine vision collection unit 4 is installed in each storage subarea 1, and the positioning information of the customer is obtained through the machine vision collection unit 4.

In the case of taking the mobile phone as the positioning information source, the customer adopts the International Mobile Equipment Identity (IMEI) or Media Access Control (MAC) code of the mobile phone held by the customer as the unique characteristic information of the customer when entering the store, and the customer is informed through sound and light, receipts, etc. The positioning information of the customer is obtained through densely distributed wireless access points (APs).

Similarly, in the case of taking the mobile phone number of the customer as the unique characteristic information of the customer, the customer is notified through sound, light, and receipt, and the positioning information of the customer is obtained through the real-time position of the mobile phone based on the base station of the service provider.

What is claimed is:

1. An open self-service sales method based on positioning of customers, comprising:
    dividing a shopping area into different shopping subareas by a purchasing isolation device, wherein the purchasing isolation device includes a plurality of isolation baffles;
    placing products in the different storage subareas by category, wherein each of the storage subareas has a unique ID code, and each customer entering a store has unique characteristic information, each of the storage subareas is provided with one of the shopping subareas in front of corresponding storage subarea, the isolation baffles are respectively mounted at two sides of each storage subarea, and the isolation baffles have a predetermined height and extend out of a rack of the storage subareas in length direction to prevent customers to pick up products from adjacent shopping subareas;

when one customer shops in one of the storage subareas, establishing a unique relationship between the storage subarea and the characteristic information of the customer, automatically weighing the products in the storage subarea before and after shopping through an automatic weighing unit of the storage subarea, respectively; calculating the quantity of selected products to generate current shopping quantity information, wherein the current shopping quantity information comprises the quantity of the selected products and an ID code of the storage subarea; and displaying the unique characteristic information of the customer by a client interface provided in each storage subarea; when there are multiple customers in one storage subarea at the same time, displaying the unique characteristic information of the customer in shopping state by the client interface;

acquiring a real-time position of the customer; determining whether the customer is shopping according to a distance between the customer and the storage subarea; if yes, generating current customer information comprising the unique characteristic information of the customer and the ID code of the storage;

acquiring the real-time position of the customer; determining whether the customer has stopped shopping according to the distance between the customer and the storage subarea; if yes, determining that the current shopping quantity information of the customer is valid;

calculating the amount of products corresponding to the current quantity information of the customer according to a unit price of the products pre-stored in the storage subarea; generating current shopping amount information comprising the amount of products and the ID code of the storage subarea;

establishing a relationship between the current shopping quantity information, the current customer information and the current shopping amount information according to the ID code of the storage subarea; and generating current shopping information;

accumulating unsettled current shopping information according to the unique characteristic information of the customer to generate a shopping list; sending the shopping list to the customer; and paying for the products in the shopping list using cash, e-banking or a third-party payment platform; and letting a guard device open to allow the customer to leave.

2. The open self-service sales method of claim 1, wherein the storage subarea has a sales state, a restock state and a return state; when the storage subarea is in a restock state, the current shopping quantity information of the customer is not generated; the storage subarea returns to the sales state after restocking is over; and when the storage subarea is in the return state, the current shopping amount information is determined to be invalid, and the customer is notified.

3. An open self-service sales system based on positioning of customers, comprising:
an open partitioned weight-sensing rack;
a positioning module configured to detect the position of the customer;
a pricing module;
a settlement module;
an access control unit; and
a central control module;
wherein the open partitioned weight-sensing rack has a plurality of storage subareas, a shopping area is divided into different shopping subareas by a purchasing isolation device, each of the storage subareas is provided with one of the shopping subareas in front of corresponding storage subarea, the purchasing isolation device includes a plurality of isolation baffles, the isolation baffles are respectively mounted at two sides of each storage subarea, and the isolation baffles have a predetermined height and extend out of a rack of the storage subareas in length direction to prevent customers to pick up products from adjacent shopping subareas, and each storage subarea is provided with a client interface; an automatic weighing unit is provided at a bottom of each of the storage subareas; a shopping subarea is provided in front of each of the storage subareas; when one customer shops in one of the storage subareas, a unique relationship is established between the storage subarea and unique characteristic information of the customer, the client interface of the storage subarea displays the unique characteristic of the customer; when there are multiple customers in one storage subarea at the same time, the client interface displays the unique characteristic information of the customer in shopping state; and the positioning module, the automatic weighing unit, the pricing module, the settlement module, and the access control unit are connected to the central control module, respectively.

4. The open self-service sales system of claim 3, wherein the positioning module is an indoor wireless positioning technology based device comprising at least one of a mobile positioning device, a Wi-Fi positioning device, a machine vision machine, a radio frequency identification (RFID) read and write device, an ultra-wideband (UWB) positioning base station, a Bluetooth positioning receiving device, an infrared positioning receiving device and an ultrasonic positioning receiving device.

5. The open self-service sales system of claim 4, wherein the positioning module further comprises an identity (ID) chip which is configured to identify the real-time position of the customer; the ID chip is carried by the customer, or the customer carries a shopping container on which the ID chip is attached.

6. The open self-service sales system of claim 5, wherein a plurality of ID chips are arranged on the shopping container at different positions.

7. The open self-service sales system of claim 4, wherein the positioning module combines machine vision and indoor wireless positioning technology, accurately verifies an identity of the customer and detects the position of the customer; and an archive containing the identity of the customer and a card corresponding to the identity of the customer is established in an entrance channel, and checking is randomly performed in the store.

8. The open self-service sales system of claim 3, characterized in that the positioning module is configured to identify the real-time position of the customer and determine whether the customer is shopping in the open partitioned weight-sensing rack according to a two-dimensional algorithm of the distance between the real-time position of the customer and the storage subarea and stay time of the customer at a current position.

9. The open self-service sales system of claim 3, wherein a camera is provided in the storage subarea; when a weight of the open self-service sales system changes, images of the storage subarea are collected by frame, and a relationship between the time when the weight of the storage subarea changes and the time when the images of the storage subarea are collected is established; and machine vision technology is adopted to identify whether a product that the customer picks on the storage subarea is consistent with the product that the customer returns to avoid abnormal exchanges.

10. The open self-service sales system of claim 3, wherein single products with different weights are placed in the storage subarea, and a product picked by the customer from the storage subarea is automatically identified according to a weight change of the storage subarea detected by the automatic weighing unit; the open self-service sales system calculates the limit of the number of different single products placed in the storage subarea and accurately identifies the picked products under the situation where a total weight is a common multiple of weights of the different single products.

11. The open self-service sales system of claim 3, wherein a channel for regular customers and a channel for new customers are provided at an entrance, or the regular customers and the new customers are automatically identified, and a training video comprising a shopping operation procedure and a training picture are provided to new customers.

12. The open self-service sales system of claim 3, wherein the automatic weighing unit has an over-range alarm function; when the weight of the products is equal to or exceed a preset range of the automatic weighing unit, the automatic weighing unit issues a prompt or an alarm.

13. The open self-service sales system of claim 3, wherein the open self-service sales system has two return modes; one mode is that the customer accurately returns a product to the original storage subarea, and the open self-service sales system recognizes, confirms and deletes the product purchased by the customer; and the other mode is that service personnel guides the customer to return the product through a special return counter.

14. The open self-service sales system of claim 3, wherein according to sales needs, a shape and a size of the shopping subarea on the automatic weighing unit are adjustable.

15. The open self-service sales system of claim 3, further comprising:
   an ID chip;
   an exit prohibition device;
   a passage isolation device;
   wherein the ID chip is configured to identify the real-time position of the customer;
   the access control unit comprises:
   an entry passage;
   an exit passage; and
   an ID chip collection and issue module;
   wherein the passage isolation device isolates a gate into the entry passage and the exit passage, and blocking bodies are respectively provided on the entry passage and the exit passage; an entrance and an exit of the entry passage are formed by the blocking bodies at both ends of the entry passage, and an entrance and an exit of the exit passage are formed by the blocking bodies at both ends of the exit passage; the access control unit is connected to the ID chip collection and issue module to control the entry and exit of the customer; the ID chip collection and issue module is configured to issue and collect an RFID tag, a UWB tag, a Bluetooth positioning signal source tag, an infrared positioning signal source tag, or an ultrasonic positioning signal source tag, and issue and collect the ID chip and a shopping container attached with the ID chip; the access control unit controls the block bodies to block the customer or let the customer pass according to issue and collection of the ID chip and a payment state corresponding to the ID chip, or issue and collection of the shopping container attached with the ID chip and a payment state corresponding to the shopping container attached with the ID chip; and the access control unit is configured to remind the customer to perform corresponding operations.

16. The open self-service sales system of claim 3, wherein each client interface comprises a voice broadcast module, a display screen, an intelligent display tag and a status indicator; the status indicator indicates the storage subarea is in different statuses through a color and a flash mode of the status indicator; the client interface is connected to the central control module; and the client interface is configured to indicate the shopping information including the characteristic information of the customer that first enters the storage subarea and is determined to be in a shopping state and issue an alarm when there is an abnormal weight change on the storage subarea; and when there are multiple customers in one storage subarea at the same time, the client interface reminds the customer in shopping state that there are multiple customers in the storage subarea.

17. The open self-service sales system of claim 3, wherein the adjacent isolation baffles have an interval of 0.4-1.5 m, and each of the isolation baffles is 0.03-0.8 m higher than products.

18. The open self-service sales system of claim 3, wherein the positioning module identifies an identity of an ID chip carried by a person to determine the person is a customer or a staff member of the store, thereby determining whether a product change is normal.

19. The open self-service sales system of claim 3, further comprising:
   an intelligent disinfection unit;
   wherein the intelligent disinfection unit is mounted around the storage subarea;
when positioning module detects that there is no person in the shopping subarea, the products in the storage subarea are disinfected by ultraviolet rays or ozone through the intelligent disinfection unit; and when the positioning module detects that a person is close to the shopping subarea, the intelligent disinfection unit automatically stops the disinfection of the products.

* * * * *